(12) United States Patent
Ferrando et al.

(10) Patent No.: US 8,257,467 B2
(45) Date of Patent: Sep. 4, 2012

(54) PROCESS FOR PARTIAL DEHYDRATION OF A GAS BY ABSORPTION ON A SOLVENT THAT CAN BE REGENERATED BY SEGREGATION AT AMBIENT TEMPERATURE

(75) Inventors: Nicolas Ferrando, Suresnes (FR); Julien Grandjean, Lyons (FR); Abdelhakim Koudil, Lyons (FR); Pascal Mougin, Rueil-Malmaison (FR); Jean-Pierre Ballaguet, Lyons (FR)

(73) Assignee: IFP Energies nouvelles, Rueil-Malmaison Cedex (FR)

( * ) Notice: Subject to any disclaimer, the term of this patent is extended or adjusted under 35 U.S.C. 154(b) by 301 days.

(21) Appl. No.: 12/637,932

(22) Filed: Dec. 15, 2009

(65) Prior Publication Data
US 2010/0154638 A1 Jun. 24, 2010

(30) Foreign Application Priority Data
Dec. 16, 2008 (FR) ...................................... 08 07055

(51) Int. Cl.
*B01D 53/14* (2006.01)
(52) U.S. Cl. ................ 95/188; 95/197; 95/206; 95/227; 95/228; 95/231; 96/236; 96/242
(58) Field of Classification Search .................... 95/188, 95/190, 206, 231, 227–229, 179; 96/234, 96/236, 242
See application file for complete search history.

(56) References Cited

U.S. PATENT DOCUMENTS

| | | | | |
|---|---|---|---|---|
| 2,151,248 A | * | 3/1939 | Vaughan | 62/632 |
| 2,228,431 A | * | 1/1941 | Archibald et al. | 203/6 |
| 2,327,187 A | * | 8/1943 | Hill | 208/346 |
| 2,794,334 A | | 6/1957 | Peaslee et al. | |
| 3,105,748 A | * | 10/1963 | Stahl | 95/191 |
| 3,349,544 A | * | 10/1967 | Scholten et al. | 95/190 |
| 4,979,966 A | | 12/1990 | Rojey et al. | |
| 5,127,231 A | * | 7/1992 | Larue et al. | 62/633 |
| 5,351,756 A | * | 10/1994 | Minkkinen et al. | 166/267 |
| 5,510,567 A | * | 4/1996 | Lermite et al. | 585/833 |
| 5,868,004 A | * | 2/1999 | Rojey et al. | 62/625 |
| 5,907,924 A | * | 6/1999 | Collin et al. | 95/194 |

(Continued)

FOREIGN PATENT DOCUMENTS

DE 2607258 A1 9/1977

(Continued)

*Primary Examiner* — Duane Smith
*Assistant Examiner* — Ives Wu
(74) *Attorney, Agent, or Firm* — Millen, White, Zelano & Branigan, P.C.

(57) ABSTRACT

A process for partial dehydration of a gas by contact with a solvent that can be regenerated by: a) A stage for absorption of $H_2O$ by contact of the gas to be treated and regenerated solvent producing a dehydrated gas effluent and a liquid solvent effluent that is charged with $H_2O$ and absorbed gas, b) A stage for cooling the solvent charged with $H_2O$ at ambient temperature, c) A stage for separation by segregation during which liquid $H_2O$ and the solvent are separated at ambient temperature, d) A stage in which the regenerated solvent that is obtained at the end of stage c) is heated, e) A stage in which the regenerated and heated solvent that is obtained at the end of stage d) is recycled to the absorption stage a).

17 Claims, 1 Drawing Sheet

U.S. PATENT DOCUMENTS

| | | | | |
|---|---|---|---|---|
| 6,016,667 A * | 1/2000 | Doerler et al. | ............... | 62/625 |
| 7,192,565 B2 * | 3/2007 | Briot et al. | ............... | 423/242.2 |
| 7,267,775 B2 * | 9/2007 | Baudot et al. | ............... | 210/652 |
| 7,718,151 B1 * | 5/2010 | Hu | ............... | 423/220 |
| 2003/0091489 A1* | 5/2003 | Hommeltoft | ............... | 423/210 |

FOREIGN PATENT DOCUMENTS

| | | |
|---|---|---|
| EP | 0068034 A1 | 1/1983 |
| EP | 0362023 A1 | 4/1990 |
| FR | 0807055 R | 8/2009 |

\* cited by examiner

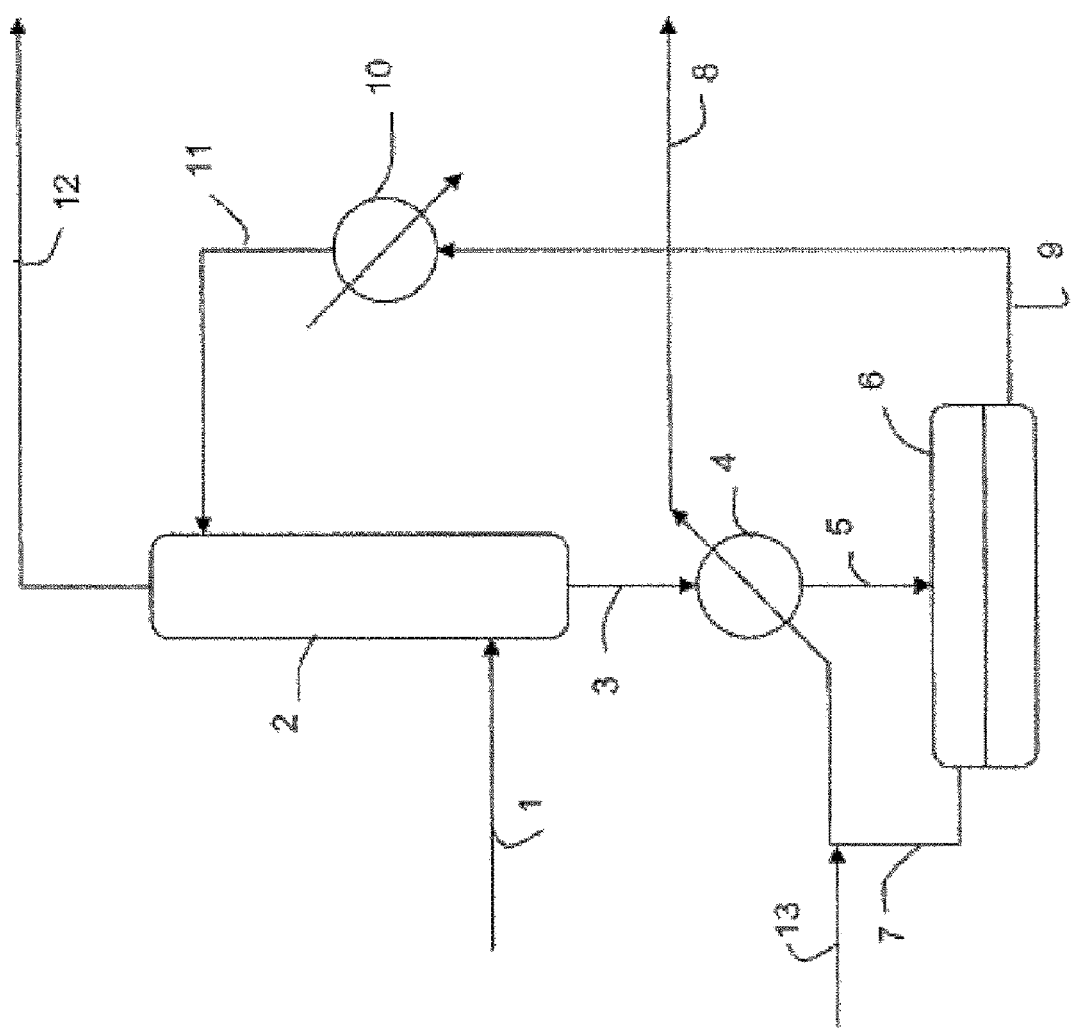

PROCESS FOR PARTIAL DEHYDRATION OF A GAS BY ABSORPTION ON A SOLVENT THAT CAN BE REGENERATED BY SEGREGATION AT AMBIENT TEMPERATURE

The invention relates to a process for partial dehydration by means of an organic solvent of a gas that contains $H_2O$ in a large quantity. The invention relates more particularly to a process that makes possible the regeneration of said solvent by a simple and economical means that does not involve any pollution of the environment. More specifically, the regeneration of the solvent is performed by separating the $H_2O$ that is extracted from the gas that is to be treated and said solvent by liquid-liquid segregation at ambient temperature. The term "ambient temperature" is defined as a temperature of between 10 and 30° C.

The process according to the invention applies particularly to the treatment of a Claus unit tail gas, natural gas, or refinery gas.

In a general way, the process according to the invention advantageously applies to any process that requires the partial dehydration of a gaseous feedstock for the purposes of improving the operation and the yield.

According to rival processes, it is common to put the gas that is to be dehydrated into contact with a hydrophilic liquid solvent. The glycols and polyglycols are part of these solvents because of their strong affinity to $H_2O$, their chemical stability, and their low cost; the triethylene glycol (TEG in abbreviated form) is used the most.

In a standard unit for dehydration of gas by a liquid solvent, for example a glycol, the wet gas enters, in a first step, the lower part of an absorption column in which it is brought into contact in counter-current with the solvent. The dehydrated gas is then extracted at the top of the absorption column and the solvent at the bottom. The solvent is then generally successively cooled, expanded and then heated before being sent into a distillation zone that makes it possible to separate $H_2O$ and solvent. The regenerated solvent is then cooled and sent to the top of the absorption column.

Different configurations that are based on this diagram have been the object of patent applications, as described in particular in the documents U.S. Pat. No. 3,105,748, FR-B-2 698 017, and U.S. Pat. No. 4,332,643.

Patent EP 1 035 904 describes a process for dehydration of a wet gas that includes two absorption zones and one zone for regeneration by distillation, whereby the regenerated solvent leaving the second absorption zone is recycled to the first zone.

The processes of the prior art are therefore based on a stage for the regeneration of solvent by thermal means, inevitably requiring a distillation stage and other expensive equipment.

The invention relates to a new process for dehydration of a gas, whereby said process comprises:

a) A stage for absorption of $H_2O$ by contact of the gas that is to be treated and the regenerated solvent that is obtained from stage e), producing a dehydrated gas effluent and a liquid solvent effluent that is charged with $H_2O$ and absorbed gas, b) A stage for cooling said solvent charged with $H_2O$ to ambient temperature, c) A stage for separation by segregation during which the $H_2O$ and the solvent are separated at ambient temperature, d) A stage in which the regenerated solvent that is obtained at the end of stage c) is heated, e) A stage in which the regenerated and heated solvent that is obtained at the end of stage d) is recycled to the absorption stage a).

The applicant developed an economical dehydration process that implements a minimum amount of equipment while having very good efficiency.

Another advantage of the process according to the invention is that it uses less expensive solvents.

The process of the invention can be applied to any humid gas, advantageously gases having a $H_2O$ content is generally between 20 and 80 mol %, especially between 30 and 80 mol %.

The implementation of the process according to the invention makes it possible to obtain a gas whose molar content of $H_2O$ is in general reduced by 10 to 50% relative to the molar content of initial $H_2O$, most often from 15 to 40%.

The solvent used in the process of the invention is any solvent that can absorb $H_2O$ at a given temperature and desorb $H_2O$ at a lower temperature, e.g. ambient temperature advantageously from any of diethyl phthalate of the chemical formula $C_{12}H_{14}O_4$ (DEP in abbreviated form), diethyl sebacate of the chemical formula $C_{14}H_{26}O_4$ (DES in abbreviated form), diethyl azelate of the chemical formula $C_{13}H_{24}O_4$, and diethyl suberate of the chemical formula $C_{12}H_{22}O_4$, preferably diethyl phthalate and diethyl sebacate, and particularly diethyl phthalate.

BRIEF DESCRIPTION OF DRAWING

The attached FIG. 1 is a schematic flowsheet of an embodiment of the invention.

The process of the invention is described in more detail below, in relation to FIG. 1.

In stage a), the wet gas that is to be treated, arriving via a line (1) at a temperature that is generally between 110 and 200° C., and preferably between 130 and 180° C., is brought into contact in an absorption column (2) with the stream of regenerated liquid solvent, arriving via a line (11), and a dehydrated gaseous effluent is extracted from the column via a line (12) to be sent, for example, to a tail gas treatment unit. The contact between the solvent and the gas is operated equally at counter-current or co-current. In general, the absorption column operates at a pressure of between 0.1 and 1 MPa, and preferably between 0.1 and 0.5 MPa. The molar ratio of the solvent/gas to be treated is generally between 0.1 and 20, and preferably between 1 and 15.

Leaving the column, a stream of $H_2O$-saturated solvent is extracted via a pipe (3) and sent into stage b) which comprise cooling the solvent that is charged with $H_2O$ at so-called ambient temperature, i.e., at a temperature of between 10 and 30° C., and preferably between 15 and 25° C. The cooling is ensured by any means that is known to one skilled in the art, preferably using an exchanger (4). The cooled gas returns via a line (5) into a separation zone (stage c)), where a liquid-liquid segregation or separation takes place in a piece of separation equipment (6), for example a sedimentation tank or any equipment that is known to one skilled in the art that makes it possible to separate a $H_2O$-rich liquid phase and a solvent-rich liquid phase. The $H_2O$-rich liquid phase is extracted via a line (7) and advantageously can be used in part as a coolant for the exchanger (4). It is then conveyed via a line (8), for example to a $H_2O$ treatment unit. The other part of the coolant that supplies the heat exchanger (4) is directed via the pipe (13).

The solvent-rich phase, also called "solvent," is extracted from the separation equipment (6) via a line (9) and is sent to a heat exchanger (10) to be brought to the operating temperature of the absorption column (2), generally operating at a temperature of between 110 and 200° C., preferably between 130 and 180° C. (stage d)). Leaving the exchanger (10), a line (11) makes it possible to recycle the regenerated and heated solvent to the absorption column (2) (stage e)). In general, the temperature difference between the operating temperature of the absorption column and that of the heated solvent is less than 10° C., and preferably less than 5° C.

The invention is further illustrated by the following non-limiting examples.

EXAMPLE 1

According to the Invention

A Claus unit effluent at a temperature of 170° C. and containing 35 mol % of $H_2O$ and the remainder incondensable gases is introduced into an absorption column according to the configuration that is described in FIG. 1, whereby the dehydrating solvent is diethyl phthalate of the chemical formula $C_{12}H_{14}O_4$. The pressure of the absorption column is 0.1 MPa. The molar ratio of solvent/gas to be treated is set at 10, and the solvent (recycled from a sedimentation tank and heated to 170° C.) contains 10 mol % of $H_2O$.

Leaving the absorption column, the solvent is cooled to a temperature of 20° C. At this temperature, a liquid-liquid separation occurs, allowing, on the one hand, the aqueous phase to be recovered, and, on the other hand, the solvent to be recovered.

Table 1 below sums up the primary compositions of the different streams: gas entering the absorption column, (recycled) solvent entering the column, dehydrated gas leaving the column, and solvent leaving the column.

TABLE 1

|  | Gas to be Dehydrated that is Entering the Column (Line 1) | Solvent Entering the Column (Line 11) | Dehydrated Gas Leaving the Column (Line 12) | Solvent Leaving the Column (Line 3) |
| --- | --- | --- | --- | --- |
| Total No. of Moles | 1.00 | 10.00 | 0.84 | 10.16 |
| No. of Mols of $H_2O$ | 0.35 | 1.00 | 0.19 | 1.16 |
| $H_2O$ Content (Mol %) | 35.0 | 10.0 | 22.6 | 11.4 |

It is demonstrated in Table 1 that it is possible, by the implementation of the process of the invention, to dehydrate a Claus unit tail gas (35 mol % of $H_2O$) and to bring it to a $H_2O$ content that is reduced by 35.4% (relative) in relation to the initial $H_2O$ content. The thus dehydrated gaseous feedstock is sent to a Clauspol® unit after having been cooled in advance to the operating temperature of this process, and the sulfur yield of the unit that is obtained is 94% by weight. The latter with a non-dehydrated feedstock by the process of the invention is 93% by weight.

EXAMPLE 2

According to the Invention

A gaseous effluent at a temperature of 160° C., containing 70 mol % of $H_2O$ and the remainder incondensable gases is introduced into an absorption column according to the configuration that is described in FIG. 1, whereby the dehydrating solvent is diethyl sebacate of the chemical formula $C_{14}H_{26}O_4$.

The pressure of the absorption column is 0.1 MPa. The molar ratio of the solvent/gas to be treated is set at 10, and the solvent (recycled from a sedimentation tank and heated to 160° C.) contains 8.5 mol % of $H_2O$.

Leaving the absorption column, the solvent is cooled to the temperature of 20° C. At this temperature, a liquid-liquid segregation occurs, and on the one hand, the aqueous phase is recovered, and, on the other hand, the solvent is recovered.

Table 2 below sums up the primary compositions of the different streams: gas entering the absorption column, (recycled) solvent entering the column, dehydrated gas leaving the column, and solvent leaving the column.

TABLE 2

|  | Gas to be Dehydrated that is Entering the Column (Line 1) | Solvent Entering the Column (Line 11) | Dehydrated Gas Leaving the Column (Line 12) | Solvent Leaving the Column (Line 3) |
| --- | --- | --- | --- | --- |
| Total No. of Moles | 1.00 | 10.00 | 0.73 | 10.27 |
| No. of Mols of $H_2O$ | 0.70 | 0.85 | 0.44 | 1.11 |
| $H_2O$ Content (Mol %) | 70.0 | 8.5 | 60.3 | 10.8 |

It is demonstrated in Table 2 that it is possible, by the implementation of the process of the invention, to dehydrate a gas that is heavily charged with $H_2O$ (70 mol %) and to bring it to a reduced $H_2O$ content of 13.8% (relative).

EXAMPLE 3

For Comparison

A Claus unit effluent at a temperature of 170° C. that contains 35 mol % of $H_2O$ and the remainder incondensable gases is introduced into an absorption column. The solvent that is introduced at the top of the column is TEG (triethylene glycol). Its temperature is 170° C. The molar ratio of solvent/gas to be treated is set at 10. The pressure of the absorption column is 0.1 MPa.

Leaving the absorption column, the solvent is cooled to the temperature of 20° C. and sent into a sedimentation tank in which $H_2O$-solvent segregation is not observed, and consequently, it therefore cannot be recycled in the absorption column.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 08/07.055, filed Dec. 16, 2008 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the dehydration of a gaseous effluent that comprises:
    a) A stage for absorption of $H_2O$ by contact of the gas that is to be treated and heated regenerated solvent obtained from stage e), producing a dehydrated gas effluent and a liquid solvent effluent charged with $H_2O$ and absorbed gas,
    b) A stage for cooling said solvent charged with $H_2O$ at ambient temperature,
    c) A stage for separation by segregation during which the $H_2O$ and the solvent are separated at ambient temperature,
    d) A stage in which the regenerated solvent obtained at the end of stage c) is heated,
    e) A stage in which the regenerated and heated solvent obtained at the end of stage d) is recycled to the absorption stage a), in which said solvent is any of diethyl phthalate of chemical formula $C_{12}H_{14}O_4$, diethyl sebacate of chemical formula $C_{14}H_{26}O_4$, diethyl azelate of chemical formula $C_{13}H_{24}O_4$, and diethyl suberate of chemical formula $C_{72}H_{22}O_4$.

2. A process according to claim 1, in which said solvent comprises at least one of diethyl phthalate and diethyl sebacate.

3. A process according to claim 1, wherein said solvent is diethyl phthalate.

4. A process according to claim 1, wherein the gaseous effluent to be treated has an $H_2O$ content of between 20 and 80 mol %.

5. A process according to claim 4, in which the $H_2O$ content of the gaseous effluent to be treated is between 30 and 80 mol %.

6. A process according to claim 1, wherein in stage b), the solvent is cooled to a temperature of between 10 and 30° C.

7. A process according to claim 6, in which in stage b), the solvent is cooled to a temperature of between 15 and 25° C.

8. A process according to claim 1, in which the gas that is to be treated is introduced in stage a) at a temperature of between 110 and 200° C.

9. A process according to claim 1, in which in stage d), the solvent is at a temperature of between 130 and 180° C.

10. A process according to claim 1, in which the $H_2O$ recovered during the separation by segregation provides coolant for stage b).

11. A process according to claim 6, in which in stage d), the solvent is at a temperature of between 130 and 180° C.

12. A process according to claim 11, in which the gas that is to be treated is introduced in stage a) at a temperature of between 110 and 200° C.

13. A process according to claim 12, in which in stage b), the solvent is cooled to a temperature of between 15 and 25° C.

14. A process according to claim 13, in which said solvent comprises at least one of diethyl phthalate and diethyl sebacate.

15. A process according to claim 13, wherein said solvent is diethyl phthalate.

16. A process according to claim 15, in which the $H_2O$ content of the gaseous effluent to be treated is between 30 and 80 mol %.

17. A process according to claim 1, wherein in (b) the $H_2O$ has a temperature of 10-30° C.

* * * * *

UNITED STATES PATENT AND TRADEMARK OFFICE
CERTIFICATE OF CORRECTION

PATENT NO.        : 8,257,467 B2                               Page 1 of 1
APPLICATION NO.   : 12/637932
DATED             : September 4, 2012
INVENTOR(S)       : Ferrando et al.

It is certified that error appears in the above-identified patent and that said Letters Patent is hereby corrected as shown below:

Column 5, line 27 reads "chemical formula $C_{72}H_{22}O_4$." should read
-- chemical formula $C_{12}H_{22}O_4$. --

Signed and Sealed this
Sixth Day of November, 2012

David J. Kappos
*Director of the United States Patent and Trademark Office*